(12) United States Patent
Landers

(10) Patent No.: US 10,045,528 B1
(45) Date of Patent: Aug. 14, 2018

(54) METHOD FOR TREATING AND PRESERVING WOOD

(71) Applicant: Phillip G Landers, Sanford, FL (US)

(72) Inventor: Phillip G Landers, Sanford, FL (US)

( * ) Notice: Subject to any disclaimer, the term of this patent is extended or adjusted under 35 U.S.C. 154(b) by 288 days.

(21) Appl. No.: 14/865,638

(22) Filed: Sep. 25, 2015

Related U.S. Application Data

(63) Continuation-in-part of application No. 14/066,836, filed on Oct. 30, 2013, now abandoned, and a continuation-in-part of application No. 13/555,947, filed on Jul. 23, 2012, now abandoned.

(60) Provisional application No. 61/510,741, filed on Jul. 22, 2011.

(51) Int. Cl.
| | | |
|---|---|---|
| *A01N 25/26* | (2006.01) | |
| *A01N 25/28* | (2006.01) | |
| *A01N 59/16* | (2006.01) | |
| *A01N 61/00* | (2006.01) | |

(52) U.S. Cl.
CPC .............. *A01N 25/28* (2013.01); *A01N 59/16* (2013.01); *A01N 61/00* (2013.01)

(58) Field of Classification Search
CPC ......... A01N 25/28; A01N 59/16; A01N 61/00
See application file for complete search history.

(56) References Cited

U.S. PATENT DOCUMENTS

| | | | |
|---|---|---|---|
| 3,615,798 A | * | 10/1971 | Woodruff ................... 523/122 |
| 4,751,947 A | | 6/1988 | Landers |
| 4,779,389 A | | 10/1988 | Landers |
| 4,773,792 A | | 11/1988 | Landers |
| 4,905,441 A | | 3/1990 | Landers |
| 5,092,375 A | | 3/1992 | Landers |
| 5,245,812 A | | 9/1993 | Landers |
| 6,237,305 B1 | | 5/2001 | Landers |
| 6,576,673 B2 | | 6/2003 | Landers |
| 6,596,204 B1 | * | 7/2003 | Landers ................... 264/4.33 |
| 6,640,506 B2 | | 11/2003 | Landers |
| 6,749,862 B2 | | 6/2004 | Landers |
| 6,908,643 B2 | | 6/2005 | Landers |
| 2003/0194454 A1 | * | 10/2003 | Bessette et al. .............. 424/745 |
| 2005/0147638 A1 | | 7/2005 | Landers |
| 2008/0020087 A1 | | 1/2008 | Landers |

OTHER PUBLICATIONS

Rothon et al. Polymer Degradation and Stability. 1996; 54: 383-385.*

* cited by examiner

*Primary Examiner* — David Browe

(74) *Attorney, Agent, or Firm* — William M. Hobby, III

(57) ABSTRACT

The wood treating composition in accordance with the present invention has a micro-encapsulating mixture of porous particles imbued with a plurality of essential oils in an epoxy polymer shell mixed in a wood coating composition containing an anionic asphalt emulsion which can release essential oil anions to form a wood preserving composition for treating and preserving wood. The process for the treatment of wood to protect the wood from decay organisms and wood destroying insects uses the composition in the treatment of wood.

1 Claim, No Drawings

METHOD FOR TREATING AND PRESERVING WOOD

This is a continuation-in-part of application Ser. No. 14/066,836, filed Oct. 30, 2013, which claims the benefit of continuation-in-part application Ser. No. 13/555,947, filed Jul. 23, 2012, which claims the benefit of provisional application Ser. No. 61/510,741, filed Jul. 22, 2011.

FIELD OF THE INVENTION

This invention relates to a composition and process for the treatment and preservation of wood against decay organisms and wood destroying insects and to the a composition and a process for the treatment and preservation of wood in which essential oils are micro-encapsulated in an epoxy polymer shell mixed in an anionic asphalt emulsion for coating wood which coating can release essential oil anions.

BACKGROUND OF THE INVENTION

Wood is often treated with toxic wood preserving chemicals when used in the construction of wooden structures such as fences, posts and telephone poles, especially wood that will be in constant contact with soil. These toxic chemical preservatives include, but are not limited to, creosote, pentachlorophenol, copper naphthenate and arsenic salts, such as copper chromated arsenic.

Wood poles make up a substantial percentage of poles used in transmission and distribution of electricity throughout the world and wood posts are commonly used to support structures such as fences. Since wood is a natural material, it is susceptible to deterioration by decay organisms especially at the ground line where the wood pole is supported in the earth. To extend the life of wood, the wood is pressure treated before installation with volatile chemicals, such as creosote, pentachlorophenol, and various combinations of arsenic salts and the like. Even though some wood is treated under pressure, the depth of penetration of the chemicals is typically limited to the outside two or three inches of the pole. When wood is placed in the ground, natural weathering allows decay organisms to flourish resulting in the formation of voids in the wood and thus a loss of structural integrity of the wood. This is especially true within the wood adjacent the ground lines where the wood enters the earth since the wood in the earth tends to absorb and accumulate moisture in the base which encourages the growth of fungi and other decay organisms. Typical methods used to arrest this decay include the application of highly toxic chemicals and fumigants that are injected into the void area created by the decay organisms. In addition, biocides are painted on the outside of the pole below the ground line to prevent additional undesirable organisms from entering the wood from the soil.

My prior U.S. Pat. No. 6,237,305 was for a method for in-situ treatment of wood utility poles that included excavating an area around the base of a wood pole supported in the earth and drilling a plurality of holes in the wood pole for injecting isophorone containing compounds thereinto. A preselected coating was used to coat a portion of the pole adjacent the excavated area with a preselected compound containing an isophorone solvent and then covering the coated portion of the pole with a covering wrap prior to refilling the excavated area around the wooden pole for treating the pole in-situ for preventing decay. The selected coating material included an isophorone solvent formulated with a wax and an acrylic resin. The method also included drilling any portion of a utility pole and injecting an isophorone compound thereinto to disperse the remaining creosote or pentachlorophenol in a treated utility pole.

Isophorone (3,5,5-trimethyl-2-cyclohexen-one-1) compounds have been shown in my U.S. Pat. No. 6,237,305 and No. 6,576,673 to be highly effective in penetrating and sealing wood. The coating migrates through moisture and is highly miscible in water and will liquify certain types of preservatives. It is used with paraffin wax to provide a water repellant barrier and surface coating on the wood. Field tests have shown that these formulations, while effective for woodpecker deterrence, does not necessarily provide long-term protection of the wood.

My prior U.S. Pat. No. 6,749,862 and No. 6,908,643 also describe surface coatings. U.S. Pat. No. 6,749,862 deters woodpeckers by blending isophorone with an epoxy resin and acrylic based sealant to form a resin composition and mixing the resin composition with a solvent resistant epoxy hardener to form a coating material.

U.S. Pat. No. 6,908,643 expands the technology and prevents animals from chewing on a structure with a composition which includes isophorone, organic-clay absorber, Bisphenol A Diglycidal Ether Polymer and polyamide resin harder. This patent expands the technology to horses and other animals with the addition of absorbers and glass flakes or mica as well as a microencapsulated acrylic resin-based sealant and a flocculated silica thickener. The primary binder of each coating is epoxy and the targets of each have been horses, woodpeckers and other animals, such as dogs.

My U.S. Pat. No. 4,905,441, is for a system for the repair of damaged wood utility poles which may have been damaged by woodpeckers. A polymer foaming agent is used to fill voids in the wood pole and to plug a passageway leading from the exterior of the pole to the void space.

The present invention is for a composition and a process for the treatment of wood to protect the wood from decay organisms and wood destroying insects. The composition includes a mixture of epoxy micro-encapsulated essential oils with a wood coating composition containing an anionic asphalt emulsion capable of producing essential oil anions therefrom when coating wood. The selected mixture is used to coat wood to protect the wood from decay organisms and wood destroying insects.

SUMMARY OF THE INVENTION

The wood treating composition in accordance with the present invention has a micro-encapsulating mixture of porous particles imbued with a plurality of essential oils in an epoxy polymer shell mixed in a wood coating composition containing an anionic asphalt emulsion to form a wood preserving composition for treating and preserving wood. The dilute asphalt emulsion will impregnate wood while capturing some of the encapsulated essential oils on the surface of the wood where it will protect the wood from decay. The composition when coated on wood releases the essential oil anions to repel insects, which have a positive charge, and prevent decay of the wood.

The method of the present invention is for the treatment of wood which includes selecting a piece of wood for treatment and making a mixture of epoxy micro-encapsulated essential oils and a wood coating composition containing an anionic asphalt emulsion. The selected wood is then coated with the mixture of the wood coating composition where some of the diluted asphalt emulsion impregnates the surface of the wood while allowing the encapsulated essential oils to collect on the surface of the wood. The micro-encapsulated essential oils protect the wood from decay organisms and wood destroying insects. The production of essential oil anions when released from the micro-encapsulating shells deter wood destroying insects having a positive charge.

More specifically the method of treating and preserving wood includes selecting porous particles for encapsulation and mixing the particles with a plurality of essential oils in an inert carrier with the selected porous particles. The mixture is micro-encapsulating to form a mixture of porous particles imbued with essential oils in an epoxy polymer shell. The essential oils micro-encapsulated in an epoxy shell is then mixed with a wood coating composition such as an anionic asphalt emulsion to form a wood preserving composition and coating. The anionic asphalt emulsion is sufficiently dilute to allow the solution to impregnate the surface of the wood while the surface of the wood captures the micro-encapsulated essential oils. A piece of wood can then be coated for treatment and protection with the wood preserving composition. The coated wood is then protected from decay organisms and wood destroying insects.

DETAILED DESCRIPTION OF AN EXEMPLARY EMBODIMENT

The present invention is a wood treating composition and method of treating wood which coats wood with a micro-encapsulating mixture of porous particles, such as diatomaceous earth, imbued with a plurality of essential oils in an epoxy polymer shell, such as an epoxy resin using an isophorone reactive diluent, mixed in a wood coating composition containing an anionic asphalt emulsion to form a wood preserving composition for treating and preserving wood. The epoxy micro-encapsulated essential oils is formed with an isophorone reactive diluent and an epoxy hardener. The anionic asphalt emulsion acts as a carrier for the polymer encapsulated essential oils. This coating also acts as a DC power source for powering an impressed current or electrolytic anode. This same energy is used to impart a negative charge (anionic energy) to the essential oils causing them to be drawn to the pests which have a positively charged smell sensor (ofactory bulb). The anionic asphalt emulsion is sufficiently dilute with water that it will soak into the wood being coated while allowing the polymer encapsulated essential oils to be filtered out onto the surface of the wood between the coating the surface of the wood.

In any sacrificial or impressed current anode it is important that an electrical connection be made between the anode, such as in this case the anionic polymer-enhanced asphalt coating, and the cathode, the wood pole, decay organisms and wood destroying insects. When used as a below ground anode around the perimeter of a wood pole, the anodic material provides direct contact across the surface of the wood pole. Carbon or graphite is typically used to diffuse the anodic current from the anode to the target cathode. In this case, the asphalt-enhanced emulsion is the carbon source that diffuses the anodic current over the surface of the wood. Thus, an anionic barrier is formed that prevents wood decay organisms from accessing wood poles. Magnesium oxide and/or zinc oxide can also be included to amplify the negative ion generation capability of the anionic polymer enhanced asphalt coating.

The method of treating wood using porous particles, such as diatomaceous earth particles, is impregnated with a mixture of essential oils and then micro-encapsulated with an anionically charged, energy absorbing epoxy polymer. Isophorone is used as a reactive diluent with the epoxy hardener in the encapsulation process. The epoxy is cured with a Lewis acid catalyst. The epoxy reaction never goes to 100% completion but continues to cross-link over time. This epoxy curing process continually releases negative ions (anionic energy). The encapsulated essential oils produce anionic energy from the epoxy curing and is used to impart, amplify and time release negatively charged essential oil fragrance molecules. The epoxy encapsulated essential oils can then be added to an asphalt emulsion, or other coating materials which is then used to coat wood to protect the wood from subterranean termites, wood-destroying insects and from rot from aerobic or anaerobic micro-organisms. The asphalt emulsion is thinned with a water or other liquid such that some of the solution will absorb into the wood surface which filters out the epoxy encapsulated essential oils which particles are too large to enter the wood, thus forming a collection or mat of encapsulated essential oils on the surface of the wood under the asphalt coating.

The method uses essential oils which are mixed with and micro-encapsulated inside small porous particles using an anionically charged polymer. The micro-encapsulated particles are micron sized particles containing anionically charged essential oils and are released over time when mixed with a wood coating composition for coating wood. Micron sized particles can be, for instance, of a mean particle size of 0.2 microns, having roughly 50% of the particles finer than 0.2 microns and 50% having a particle size larger than 0.2 microns.

An essential oil is a concentrated liquid containing volatile aroma compounds from plants. It is essential in the sense that it contains the essence of the plant's fragrance. They are generally extracted from the plants by distillation especially using steam but may be extracted by other methods such as solvent extraction. Essential oils used herein include, but are not limited to, cedar oil, cinnamon oil, citrus terpenes, lemongrass oil, mint oil, peppermint oil, rosemary oil and thyme oil.

Diatomaceous earth is a light friable siliceous material derived chiefly from diatom remains and used especially in filters and as an abrasive.

Micro-encapsulation in the present invention utilizes my prior U.S. Pat. No. 6,596,204 dated Jul. 22, 2003 for Method of Encapsulating a Volatile Liquid which is incorporated herein by reference in its entirety. This patent is for a process of micro-encapsulating a liquid which process includes selecting and mixing a liquid with porous clay or ceramic particles for encapsulating the liquid. The mixed liquid and porous particles are mixed and a vacuum may be applied to the mixture to impregnate the liquid in the porous particles. Essential oils are mixed with porous particles to saturate the particles. The epoxy resin and a Lewis acid catalyst is then added to the mixture for forming a resin cured shell around the porous particles to micro-encapsulate the essential oils in the porous particles. The resin only cures on the outer shell of the porous particles when coming into contact with the Lewis acid catalyst and supports the liquid essential oils in the porous particles.

The process for encapsulating the essential oils includes the selection of porous particles which would normally be porous clay or ceramic particles but a preferred material is diatomaceous earth having a particle size of from a few microns to ¼ inch in diameter. A diatomaceous earth is used for absorbing the essential oils prior to encapsulating the essential oil saturated diatomaceous earth.

An essential oil or oils are next selected which might include various combinations from the group of cedar oil, cinnamon oil, citrus terpenes, lemongrass oil, mint oil, peppermint oil, rosemary oil, spearmint oil and/or thyme oil.

The combination of essential oils selected is used in a total concentration of less than 1% in a carrier of inert ingredients forming 99+% of the mixture. Inert ingredients might include water, isopropanol, soy bean oil, isophorone, stannous chloride and vanillin. Isophorone is the preferred reactive diluent.

The selected essential oils in the inert liquid and the porous particles, such as diatomaceous earth, are then mixed to form a dilute combination of essential oils.

The selected porous particles imbued with selected essential oils in a carrier liquid is then micro-encapsulated. This is accomplished in accordance with my U.S. Pat. No. 6,596,204 by adding a polymer catalyst for a polymer resin, such as an epoxy catalyst for an epoxy resin to form a resin cured shell around the porous particles to micro-encapsulate particles holding the particles saturated with essential oil therein. A Lewis acid catalyst is the preferred catalyst in the present process.

The micro-encapsulated essential oils in the diatomaceous earth particles is then mixed with a wood coating composition having carbon therein, such as asphalt or an anionic asphalt emulsion. This mixture is then ready to coat and treat wood to protect the wood against decay organisms and wood destroying insects, such as termites. This results from the continual release of negative ions or anions from the continually curing epoxy and the release of the micro-encapsulated essential oils which is amplified by the anionic energy imparted to the time released negatively charged essential oils. The encapsulated particles release the negatively charged ions which when contacting the pest's positively charged olfactory bulb and neurological system disorients and repels the pest. This action takes place when the two opposite charges come into sufficient proximity.

The micro-sized particles in this application may generally have a mean particle size of around 0.2 microns, typically having 50% of the particles finer than 0.2 microns and roughly 50% of the particles larger than 0.2 microns. These particles are large enough that they will not penetrate into a wood surface being coated and some will be filtered out of the liquid coating being absorbed into the wood.

In one example diatomaceous earth particles sized from 3 microns to ¼ inch are saturated with a mixture including essential oils as follows:

| | |
|---|---|
| Cedar Oil | 0.08% |
| Cinnamon Oil | 0.10% |
| Clove Oil | 0.09% |
| Lemongrass Oil | 0.08% |
| Peppermint Oil | 0.07% |
| Rosemary Oil | 0.06% |
| Spearmint Oil | 0.08% |
| Thyme Oil | 0.06% |
| Inert Ingredients | 99.38% |
| Total | 100.00% |

The inert ingredients in the example include isophorone, isopropanol, soy bean oil, vanillin and water. The diatomaceous earth is imbued with the mixture of essential oils, a polymer hardener and inert ingredients and then micro-encapsulated using a Lewis acid catalyst formed with an isophorone reactive diluent and an epoxy hardener. The particles are then mixed with an anionic asphalt emulsion which is used to coat and protect wood such as a portion of a wood pole in the earth. Magnesium oxide and/or zinc oxide can also be included to amplify the negative ion generation capability of the particles.

The treatment of wood in accordance with the present process is well suited to the in-situ treatment of wood utility poles. The wood poles supported in the earth may be excavated therearound and the base of the pole coated with the present wood coating composition on the portion extending below the earth and for a short distance above the ground, such as 18 inches above the ground line. The coating includes a mixture of epoxy micro-encapsulated essential oils and a wood coating composition of the present invention and is used to coat a portion of the pole adjacent the excavated area with the composition prior to refilling the excavated area around the wooden pole for treating the pole in-situ for preventing decay and termite infestation.

It should be clear at this time that a composition and method for treating wood and especially wood which may be in contact with the earth has been provided. However the present invention is not to be considered limited to the forms shown which are to be considered illustrative rather than restrictive.

I claim:

1. A method of treating and preserving wood comprising the steps of:

selecting porous particles for encapsulation;

selecting a plurality of essential oils;

mixing said selected plurality of essential oils in an inert carrier with the selected porous particles;

micro-encapsulating said mixture of porous particles imbued with said essential oils in an epoxy polymer shell, in which the essential oils are sized to prevent absorption into the surface of the wood being treated;

mixing said micro-encapsulated mixture with a wood coating composition containing an anionic carbon emulsion diluted for partial absorption into the surface of wood to form a wood preserving composition;

mixing magnesium oxide into said wood preserving composition;

selecting a piece of wood for treatment with said wood preserving composition; and coating the selected wood with said wood preserving composition' whereby said coated wood is protected from decay organisms and wood destroying insects.

\* \* \* \* \*